United States Patent
Grether et al.

(10) Patent No.: US 9,580,435 B2
(45) Date of Patent: Feb. 28, 2017

(54) PYRROLO[2,3-D]PYRIMIDINE DERIVATIVES AS CB2 RECEPTOR AGONISTS

(71) Applicant: Hoffman-La Roche Inc., Little Falls, NJ (US)

(72) Inventors: Uwe Grether, Efringen-Kirchen (DE); Atsushi Kimbara, Shizuoka (JP); Matthias Nettekoven, Grenzach-Wyhlen (DE); Stephan Roever, Inzlingen (DE); Mark Rogers-Evans, Bottmingen (CH); Tanja Schulz-Gasch, Ziefen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/923,186

(22) Filed: Oct. 26, 2015

(65) Prior Publication Data

US 2016/0046637 A1    Feb. 18, 2016

Related U.S. Application Data

(63) Continuation of application No. PCT/US2014/058648, filed on Apr. 29, 2014.

(30) Foreign Application Priority Data

May 2, 2013    (EP) .................................... 13166296

(51) Int. Cl.
*A61K 31/519*    (2006.01)
*C07D 487/04*    (2006.01)
*C07D 519/00*    (2006.01)

(52) U.S. Cl.
CPC ........... *C07D 487/04* (2013.01); *C07D 519/00* (2013.01)

(58) Field of Classification Search
CPC .......................... C07D 487/04; C07D 519/00
See application file for complete search history.

(56) References Cited

U.S. PATENT DOCUMENTS

2012/0316147 A1    12/2012 Bissantz

FOREIGN PATENT DOCUMENTS

| WO | 01/58869 A2 | 8/2001 |
|---|---|---|
| WO | 03/082191 A2 | 10/2003 |
| WO | 03/093269 A2 | 11/2003 |
| WO | 2004/058767 A1 | 7/2004 |
| WO | 2006/047516 A2 | 5/2006 |
| WO | 2008/141239 A1 | 11/2008 |
| WO | 2009/032754 A2 | 3/2009 |
| WO | 2009/051705 A1 | 4/2009 |
| WO | 2010/118367 A2 | 10/2010 |
| WO | 2011/045702 A1 | 4/2011 |
| WO | 2013/068306 A1 | 5/2013 |
| WO | 2014/005968 A1 | 1/2014 |
| WO | 2014/086705 A1 | 6/2014 |
| WO | 2014/086805 A1 | 6/2014 |
| WO | 2014/086806 A1 | 6/2014 |
| WO | 2014/086807 | 6/2014 |
| WO | 2014/135507 A1 | 9/2014 |
| WO | 2014/177490 A1 | 11/2014 |

OTHER PUBLICATIONS

Cheng et al., "Potential Purine Antagonists VII. Synthesis of 6-Alkylpyrazolo[3,4-d]pyrimidines" Journal of Organic Chemistry 23:191-200 ( 1958).
Cheng et al., "Potential Purine Antagonists. XII. Synthesis of 1-Alkyl(aryl)-4,6-disubstituted Pyra~olo(3,4-d]pyrimidines" Journal of Organic Chemistry 23:852-861 ( 1958).
ISR for PCT/EP2014/058648.
Nettekoven et al., "Highly potent and selective cannabinoid receptor 2 agonists: initial hit optimization of an adamantyl hit series identified from high-through-put screening" Bioorg Med Chem Lett. 23(5):1177-81 ( 2013).
Nettekoven et al., "Novel Triazolopyrimidine-Derived Cannabinoid Receptor 2 Agonists as Potential Treatment for Inflammatory Kidney Diseases" ChemMedChem. 11(2):179-189 (2016).
Senga et al., "Synthesis and Xanthine Oxidase Inhibitory Activity of 4,6-Disubstituted 1-p-Chlorophenylpyrazolo[3,4-d]pyrimidines" Journal of Hererocyclic Chemistry 19(6):1565:67 ( 1982).
Slavik et al., "Discovery of a high affinity and selective pyridine analog as a potential positron emission tomography imaging agent for cannabinoid type 2 receptor" J Med Chem. 58(10):4266-77 (2015).

*Primary Examiner* — Brian McDowell
(74) *Attorney, Agent, or Firm* — Alex Andrus

(57) ABSTRACT

The invention relates to a compound of formula (I)

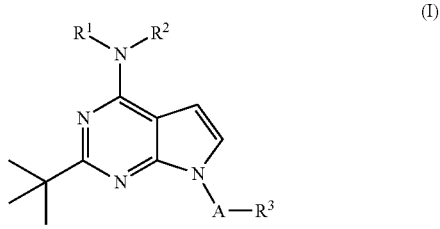

wherein A and $R^1$ to $R^3$ are defined as in the description and in the claims. The compound of formula (I) can be used as a medicament.

11 Claims, No Drawings

PYRROLO[2,3-D]PYRIMIDINE DERIVATIVES AS CB2 RECEPTOR AGONISTS

CROSS REFERENCE TO RELATED APPLICATIONS

This application is a continuation of International Application No. PCT/EP2014/058648 having an International Filing Date of 29 Apr. 2014, the entire contents of which are incorporated herein by reference, and which claims the benefit of priority under U.S.C. §119 to EP 13166296.7, filed 2 May 2013.

FIELD OF THE INVENTION

The present invention relates to organic compounds useful for therapy and/or prophylaxis in a mammal, and in particular to compounds that are preferential agonists of the Cannabinoid Receptor 2.

SUMMARY OF THE INVENTION

The invention relates in particular to a compound of formula (I)

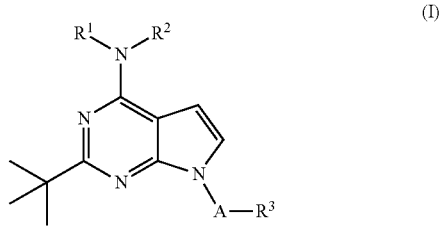

wherein
A is $CH_2$ or absent;
$R^1$ and $R^2$, together with the nitrogen atom to which they are attached form substituted pyrrolidinyl or 2-oxa-6-azaspiro[3.3]heptyl, wherein substituted pyrrolidinyl is pyrrolidinyl substituted with one or two substituents independently selected from halogen, hydroxyl and alkylcarbonyloxy; and
$R^3$ is halophenyl, alkylsulfonylphenyl, haloalkylphenyl, halopyridinyl, alkyloxadiazolyl, alkyltriazolyl, alkyltetrazolyl, oxolanyl, cycloalkyltetrazolyl or haloalkyl-1H-pyrazolyl;
or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

DEFINITIONS

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. A particular example of alkyl is methyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular example of "cycloalkyl" is cyclopropyl.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. Particular "halogen" are fluorine and chlorine. In the definition of $R^1$ and $R^2$, fluorine is a particular halogen.

The term "haloalkyl", alone or in combination, denotes an alkyl group substituted with at least one halogen, particularly substituted with one to five halogens, particularly one to three halogens. A particular "haloalkyl" is trifluoromethyl.

The terms "hydroxyl" and "hydroxy", alone or in combination, signify the —OH group.

The term "carbonyl", alone or in combination, signifies the —C(O)— group.

The term "oxy", alone or in combination, signifies the —O— group.

The term "amino", alone or in combination, signifies the primary amino group (—NH$_2$), the secondary amino group (—NH—), or the tertiary amino group (—N—). A particular amino is —NH—.

The term "sulfonyl", alone or in combination, signifies the —S(O)$_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

DETAILED DESCRIPTION OF EXEMPLARY EMBODIMENTS

The invention relates in particular to:

A compound of formula (I) wherein A is $CH_2$;

A compound of formula (I) wherein $R^1$ and $R^2$, together with the nitrogen atom to which they are attached form substituted pyrrolidinyl, wherein substituted pyrrolidinyl is pyrrolidinyl substituted with one or two substituents independently selected from halogen and hydroxyl;

A compound of formula (I) wherein $R^1$ and $R^2$, together with the nitrogen atom to which they are attached form substituted pyrrolidinyl, wherein substituted pyrrolidinyl is pyrrolidinyl substituted with one or two substituents independently selected from fluorine and hydroxyl;

A compound of formula (I) wherein $R^1$ and $R^2$, together with the nitrogen atom to which they are attached form difluoropyrrolidinyl or hydroxypyrrolidinyl;

A compound of formula (I) wherein $R^1$ and $R^2$, together with the nitrogen atom to which they are attached form difluoropyrrolidinyl, 2-oxa-6-azaspiro[3.3]heptyl, hydroxypyrrolidinyl or methylcarbonyloxypyrrolidinyl;

A compound of formula (I) wherein $R^3$ is halophenyl, haloalkylphenyl, alkylsulfonylphenyl, halopyridinyl or alkyloxadiazolyl;

A compound of formula (I) wherein $R^3$ is dichlorophenyl, chlorofluorophenyl, trifluoromethylphenyl, methylsulfonylphenyl, chloropyridinyl or methyloxadiazolyl; and A compound of formula (I) wherein $R^3$ is chlorophenyl, dichlorophenyl, chlorofluorophenyl, methylsulfonylphenyl, trifluoromethylphenyl, chloropyridinyl, methyloxadiazolyl, dimethyltriazolyl, methyltetrazolyl, cyclopropyltetrazolyl, oxolanyl or trifluoromehtyl-1H-pyrazolyl.

The invention further relates to a compound of formula (I) selected from:

2-tert-butyl-7-[(2-chlorophenyl)methyl]-4-(3,3-difluoropyrrolidin-1-yl)pyrrolo[2,3-d]pyrimidine;
2-tert-butyl-7-[(2-chloro-4-fluorophenyl)methyl]-4-(3,3-difluoropyrrolidin-1-yl)pyrrolo[2,3-d]pyrimidine;
2-tert-butyl-4-(3,3-difluoropyrrolidin-1-yl)-7-[(2-methylsulfonylphenyl)methyl]pyrrolo[2,3-d]pyrimidine;
2-tert-butyl-4-(3,3-difluoropyrrolidin-1-yl)-7-[[2-(trifluoromethyl)phenyl]methyl]pyrrolo[2,3-d]pyrimidine;
2-tert-butyl-7-[(2,3-dichlorophenyl)methyl]-4-(3,3-difluoropyrrolidin-1-yl)pyrrolo[2,3-d]pyrimidine;
2-tert-butyl-7-[(2-chloropyridin-3-yl)methyl]-4-(3,3-difluoropyrrolidin-1-yl)pyrrolo[2,3-d]pyrimidine;
2-tert-butyl-7-[(3-chloropyridin-2-yl)methyl]-4-(3,3-difluoropyrrolidin-1-yl)pyrrolo[2,3-d]pyrimidine;
5-[[2-tert-butyl-4-(3,3-difluoropyrrolidin-1-yl)pyrrolo[2,3-d]pyrimidin-7-yl]methyl]-3-methyl-1,2,4-oxadiazole;
3-[[2-tert-butyl-4-(3,3-difluoropyrrolidin-1-yl)pyrrolo[2,3-d]pyrimidin-7-yl]methyl]-4-methyl-1,2,5-oxadiazole;
2-[[2-tert-butyl-4-(3,3-difluoropyrrolidin-1-yl)pyrrolo[2,3-d]pyrimidin-7-yl]methyl]-5-methyl-1,3,4-oxadiazole;
2-tert-butyl-4-(3,3-difluoropyrrolidin-1-yl)-7-[(4,5-dimethyl-1,2,4-triazol-3-yl)methyl]pyrrolo[2,3-d]pyrimidine;
2-tert-butyl-4-(3,3-difluoropyrrolidin-1-yl)-7-[(1-methyltetrazol-5-yl)methyl]pyrrolo[2,3-d]pyrimidine;
2-tert-butyl-7-[(1-cyclopropyltetrazol-5-yl)methyl]-4-(3,3-difluoropyrrolidin-1-yl)pyrrolo[2,3-d]pyrimidine;
6-[2-tert-butyl-7-[(2-chlorophenyl)methyl]pyrrolo[2,3-d]pyrimidin-4-yl]-2-oxa-6-azaspiro[3.3]heptane;
6-[2-tert-butyl-7-[(3-methyl-1,2,4-oxadiazol-5-yl)methyl]pyrrolo[2,3-d]pyrimidin-4-yl]-2-oxa-6-azaspiro[3.3]heptane;
6-[2-tert-butyl-7-[(3S)-oxolan-3-yl]pyrrolo[2,3-d]pyrimidin-4-yl]-2-oxa-6-azaspiro[3.3]heptane;
6-[2-tert-butyl-7-[(3R)-oxolan-3-yl]pyrrolo[2,3-d]pyrimidin-4-yl]-2-oxa-6-azaspiro[3.3]heptane;
6-[2-tert-butyl-7-[(2-chloro-4-fluorophenyl)methyl]pyrrolo[2,3-d]pyrimidin-4-yl]-2-oxa-6-azaspiro[3.3]heptane;
6-[2-tert-butyl-7-[(2-methylsulfonylphenyl)methyl]pyrrolo[2,3-d]pyrimidin-4-yl]-2-oxa-6-azaspiro[3.3]heptane;
6-[2-tert-butyl-7-[(2-chloropyridin-3-yl)methyl]pyrrolo[2,3-d]pyrimidin-4-yl]-2-oxa-6-azaspiro[3.3]heptane;
6-[2-tert-butyl-7-[(2,3-dichlorophenyl)methyl]pyrrolo[2,3-d]pyrimidin-4-yl]-2-oxa-6-azaspiro[3.3]heptane;
6-[2-tert-butyl-7-[(4-methyl-1,2,5-oxadiazol-3-yl)methyl]pyrrolo[2,3-d]pyrimidin-4-yl]-2-oxa-6-azaspiro[3.3]heptane;
6-[2-tert-butyl-7-[(5-methyl-1,3,4-oxadiazol-2-yl)methyl]pyrrolo[2,3-d]pyrimidin-4-yl]-2-oxa-6-azaspiro[3.3]heptane;
1-[2-tert-butyl-7-[(2-chlorophenyl)methyl]pyrrolo[2,3-d]pyrimidin-4-yl]pyrrolidin-3-ol;
1-[2-tert-butyl-7-[(2-chloro-4-fluorophenyl)methyl]pyrrolo[2,3-d]pyrimidin-4-yl]pyrrolidin-3-ol;
1-[2-tert-butyl-7-[(2-methylsulfonylphenyl)methyl]pyrrolo[2,3-d]pyrimidin-4-yl]pyrrolidin-3-ol;
1-[2-tert-butyl-7-[[2-(trifluoromethyl)phenyl]methyl]pyrrolo[2,3-d]pyrimidin-4-yl]pyrrolidin-3-ol;
1-[2-tert-butyl-7-[(2,3-dichlorophenyl)methyl]pyrrolo[2,3-d]pyrimidin-4-yl]pyrrolidin-3-ol;
1-[2-tert-butyl-7-[(2-chloropyridin-3-yl)methyl]pyrrolo[2,3-d]pyrimidin-4-yl]pyrrolidin-3-ol;
1-[2-tert-butyl-7-[(3-chloropyridin-2-yl)methyl]pyrrolo[2,3-d]pyrimidin-4-yl]pyrrolidin-3-ol;
1-[2-tert-butyl-7-[(3-methyl-1,2,4-oxadiazol-5-yl)methyl]pyrrolo[2,3-d]pyrimidin-4-yl]pyrrolidin-3-ol;
1-[2-tert-butyl-7-[(4-methyl-1,2,5-oxadiazol-3-yl)methyl]pyrrolo[2,3-d]pyrimidin-4-yl]pyrrolidin-3-ol;
1-[2-tert-butyl-7-[(5-methyl-1,3,4-oxadiazol-2-yl)methyl]pyrrolo[2,3-d]pyrimidin-4-yl]pyrrolidin-3-ol;
1-[2-tert-butyl-7-[(1-methyltetrazol-5-yl)methyl]pyrrolo[2,3-d]pyrimidin-4-yl]pyrrolidin-3-ol;
[1-[2-tert-butyl-7-[(1-methyltetrazol-5-yl)methyl]pyrrolo[2,3-d]pyrimidin-4-yl]pyrrolidin-3-yl]acetate;
[1-[2-tert-butyl-7-[(2,3-dichlorophenyl)methyl]pyrrolo[2,3-d]pyrimidin-4-yl]pyrrolidin-3-yl]acetate;
[1-[2-tert-butyl-7-[(4-methyl-1,2,5-oxadiazol-3-yl)methyl]pyrrolo[2,3-d]pyrimidin-4-yl]pyrrolidin-3-yl]acetate;
1-[2-tert-butyl-7-[(1-cyclopropyltetrazol-5-yl)methyl]pyrrolo[2,3-d]pyrimidin-4-yl]pyrrolidin-3-ol;

1-[2-tert-butyl-7-[(3R)-oxolan-3-yl]pyrrolo[2,3-d]pyrimidin-4-yl]pyrrolidin-3-ol;
1-[2-tert-butyl-7-[[3-(trifluoromethyl)-1H-pyrazol-4-yl]methyl]pyrrolo[2,3-d]pyrimidin-4-yl]pyrrolidin-3-ol;
2-tert-butyl-4-(3,3-difluoropyrrolidin-1-yl)-7-[[3-(trifluoromethyl)-1H-pyrazol-4-yl]methyl]pyrrolo[2,3-d]pyrimidine;
(3S)-1-[2-tert-butyl-7-[(2,3-dichlorophenyl)methyl]pyrrolo[2,3-d]pyrimidin-4-yl]pyrrolidin-3-ol;
(3S)-1-[2-tert-butyl-7-[(2-chloro-4-fluorophenyl)methyl]pyrrolo[2,3-d]pyrimidin-4-yl]pyrrolidin-3-ol;
(3S)-1-[2-tert-butyl-7-[[2-(trifluoromethyl)phenyl]methyl]pyrrolo[2,3-d]pyrimidin-4-yl]pyrrolidin-3-ol;
(3S)-1-[2-tert-butyl-7-[(2-methylsulfonylphenyl)methyl]pyrrolo[2,3-d]pyrimidin-4-yl]pyrrolidin-3-ol;
(3S)-1-[2-tert-butyl-7-[(2-chloropyridin-3-yl)methyl]pyrrolo[2,3-d]pyrimidin-4-yl]pyrrolidin-3-ol;
(3S)-1-[2-tert-butyl-7-[(3-chloropyridin-2-yl)methyl]pyrrolo[2,3-d]pyrimidin-4-yl]pyrrolidin-3-ol;
(3S)-1-[2-tert-butyl-7-[(4-methyl-1,2,5-oxadiazol-3-yl)methyl]pyrrolo[2,3-d]pyrimidin-4-yl]pyrrolidin-3-ol;
6-[2-tert-butyl-7-[(3-chloropyridin-2-yl)methyl]pyrrolo[2,3-d]pyrimidin-4-yl]-2-oxa-6-azaspiro[3.3]heptane; and
6-[2-tert-butyl-7-[(1-methyltetrazol-5-yl)methyl]pyrrolo[2,3-d]pyrimidin-4-yl]-2-oxa-6-azaspiro[3.3]heptane.

The invention further relates to a compound of formula (I) selected from:
2-tert-butyl-4-(3,3-difluoropyrrolidin-1-yl)-7-[[2-(trifluoromethyl)phenyl]methyl]pyrrolo[2,3-d]pyrimidine;
2-tert-butyl-7-[(3-chloropyridin-2-yl)methyl]-4-(3,3-difluoropyrrolidin-1-yl)pyrrolo[2,3-d]pyrimidine;
3-[[2-tert-butyl-4-(3,3-difluoropyrrolidin-1-yl)pyrrolo[2,3-d]pyrimidin-7-yl]methyl]-4-methyl-1,2,5-oxadiazole;
1-[2-tert-butyl-7-[[2-(trifluoromethyl)phenyl]methyl]pyrrolo[2,3-d]pyrimidin-4-yl]pyrrolidin-3-ol;
1-[2-tert-butyl-7-[(2-chloropyridin-3-yl)methyl]pyrrolo[2,3-d]pyrimidin-4-yl]pyrrolidin-3-ol;
1-[2-tert-butyl-7-[(3-chloropyridin-2-yl)methyl]pyrrolo[2,3-d]pyrimidin-4-yl]pyrrolidin-3-ol;
(3S)-1-[2-tert-butyl-7-[(2,3-dichlorophenyl)methyl]pyrrolo[2,3-d]pyrimidin-4-yl]pyrrolidin-3-ol;
(3S)-1-[2-tert-butyl-7-[(2-chloro-4-fluorophenyl)methyl]pyrrolo[2,3-d]pyrimidin-4-yl]pyrrolidin-3-ol;
(3S)-1-[2-tert-butyl-7-[[2-(trifluoromethyl)phenyl]methyl]pyrrolo[2,3-d]pyrimidin-4-yl]pyrrolidin-3-ol;
(3S)-1-[2-tert-butyl-7-[(2-methylsulfonylphenyl)methyl]pyrrolo[2,3-d]pyrimidin-4-yl]pyrrolidin-3-ol;
(3S)-1-[2-tert-butyl-7-[(2-chloropyridin-3-yl)methyl]pyrrolo[2,3-d]pyrimidin-4-yl]pyrrolidin-3-ol;
(3S)-1-[2-tert-butyl-7-[(3-chloropyridin-2-yl)methyl]pyrrolo[2,3-d]pyrimidin-4-yl]pyrrolidin-3-ol; and
(3S)-1-[2-tert-butyl-7-[(4-methyl-1,2,5-oxadiazol-3-yl)methyl]pyrrolo[2,3-d]pyrimidin-4-yl]pyrrolidin-3-ol.

The synthesis of the compound of formula (I) can, for example, be accomplished according to the following schemes.

Unless otherwise indicated, A and $R^1$ to $R^3$ have the meaning as defined above.

The preparation of compounds of formula I of the present invention may be carried out in sequential or convergent synthetic routes. Syntheses of the compounds of the invention are shown in the following scheme. The skills required for carrying out the reactions and purifications of the resulting products are known to those skilled in the art. The substituents and indices used in the following description of the processes have the significance given herein before unless indicated to the contrary. In more detail, the compounds of formula I can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

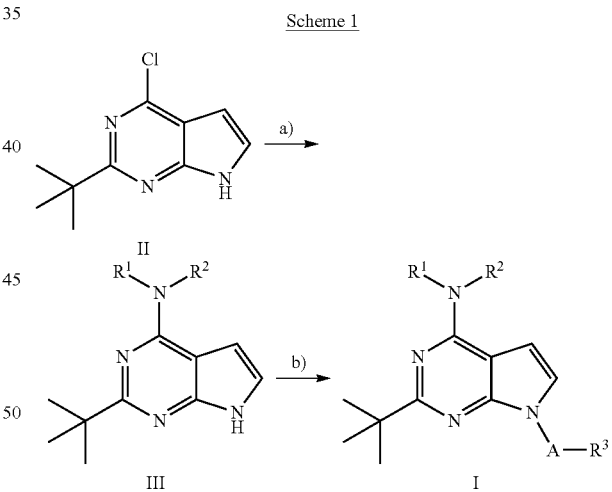

Scheme 1 a) 2-tert-Butyl-4-chloro-7H-pyrrolo[2,3-d]pyrimidine II is commercially available and can conveniently be reacted with an amine (commercially available, or known in the art) in the presence or the absence of a base to afford intermediate III.

b) Intermediate III can conveniently be reacted with an electrophile (commercially available, or known in the art) in the presence or absence of a base to yield title compound (I).

Any protecting group used in the sequence can either be cleaved subsequent to step a) or b).

The invention thus relates to a process for the preparation of a compound of formula (I), comprising the reaction of a compound of formula (A)

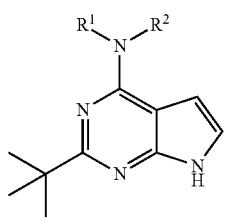

(A)

in the presence of X-A-R³, wherein X is a leaving group and wherein A and R¹ to R³ are as defined above.

In the process of the invention, suitable leaving groups are for example chlorine or bromine.

The process of the invention can be carried out in the presence of a base. Examples of suitable bases are NaH or KOtBu.

The process of the invention can be carried out for example in NMP (N-Methyl-2-pyrrolidone), DMF (dimethylformamide) or THF (tetrahydrofurane).

The invention also relates to a compound of formula (I) when manufactured according to the above process.

The invention also relates in particular to:

The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis;

A compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention particularly relates to a compound of formula (I) for the treatment or prophylaxis of myocardial infarction.

The invention further particularly relates to a compound of formula (I) for the treatment or prophylaxis of age-related macular degeneration, diabetic retinopathy, glaucoma, retinal vein occlusion, retinopathy of prematurity, ocular ischemic syndrome, geographic atrophy or uveitis.

The invention further particularly relates to a compound of formula (I) for the treatment or prophylaxis of amyotrophic lateral sclerosis or multiple sclerosis.

The invention is further directed to a compound of formula (I), when manufactured according to a process according to the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Example 1

2-tert-butyl-7-[(2-chlorophenyl)methyl]-4-(3,3-difluoropyrrolidin-1-yl)pyrrolo[2,3-d]pyrimidine

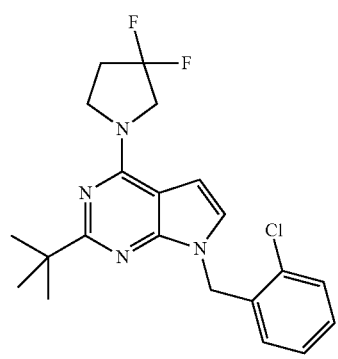 [SMILES: CC(C)(C)c1nc(N2CCC(F)(F)C2)c2ccn(Cc3ccccc3Cl)c2n1]

a) 2-tert-Butyl-1,7-dihydro-pyrrolo[2,3-d]pyrimidin-4-one

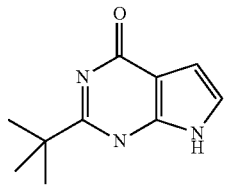

To a solution of sodium ethoxide (210 mL, 563 mmol; 21% in EtOH) in absolute EtOH (290 mL) were added ethyl-2-cyano-4,4-diethoxybutanoate (45 g, 281 mmol) and 2,2-dimethyl-propionamidine (59 g, 256 mmol) and heated to reflux for 12 h. The mixture was concentrated, the residue was diluted with water (100 mL) and acidified (pH 6-7) with aqueous 2N HCl solution. The precipitate was filtered, dried under vacuum and dissolved in EtOH (100 mL). $H_2SO_4$ (10 mL) was added at 0° C. and the mixture was heated to reflux for 2 h. After cooling to 25° C. the solution was made basic (pH-8-9) with $NH_3$ aq. The precipitate was filtered and dried under vacuum to yield 2-tert-butyl-1,7-dihydro-pyrrolo[2,3-d]pyrimidin-4-one (18 g, 47%) as white solid which was used in the next step without further purification. MS (m/e): 192 (M+H).

b) 2-tert-Butyl-4-chloro-7H-pyrrolo[2,3-d]pyrimidine

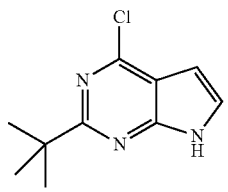

A mixture of 2-tert-butyl-1,7-dihydro-pyrrolo[2,3-d]pyrimidin-4-one (2.5 g, 13 mmol) and $POCl_3$ (10 mL) was refluxed for 3 h. After cooling to 25° C. ice-water (40 mL) was added and the aqueous layer was extracted with EtOAc (2×75 mL). The combined organic layers were washed with water (4×50 mL) and brine (40 mL), dried over anhydrous $Na_2SO_4$, filtered and concentrated in vacuo. The residue was purified by column chromatography over flash silica gel (50% EtOAc/hexane) to yield after evaporation of the product containing fractions the title compound (1.2 g, 44%) as light yellow solid. MS (m/e): 210.4 (M+H).

c) 2-tert-Butyl-4-(3,3-difluoro-pyrrolidin-1-yl)-7H-pyrrolo[2,3-d]pyrimidine

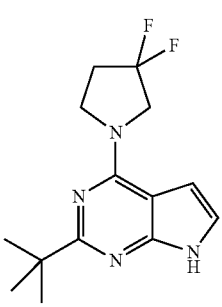 [SMILES: CC(C)(C)c1nc(N2CCC(F)(F)C2)c2cc[nH]c2n1]

To a solution of 2-tert-butyl-4-chloro-7H-pyrrolo[2,3-d]pyrimidine (1 g, 4.7 mmol), 3,3-difluoro-pyrrolidine hydrochloride (1.1 g, 7.18 mmol) and DIPEA (3 ml, 14.1 mmol) in EtOH (15 mL) was stirred at 100° C. in a sealed tube for 16 h. The volatilities were removed in vacuo and the residue dissolved in DCM (20 mL). The mixture was washed with water (2×10 mL), brine (10 mL), dried over anhydrous Na$_2$SO$_4$, filtered and evaporated under reduced pressure. The residue was purified by column chromatography over silica eluting with 20% EtOAc/hexane to yield the title compound (1 g, 74%) as off white solid. MS (m/e): 280.8 (M+H).

d) 2-tert-butyl-7-[(2-chlorophenyl)methyl]-4-(3,3-difluoropyrrolidin-1-yl)pyrrolo[2,3-d]pyrimidine A solution of 2-tert-butyl-4-(3,3-difluoro-pyrrolidin-1-yl)-7H-pyrrolo[2,3-d]pyrimidine (50 mg, 0.17 mmol), potassium tert-butoxide (31 mg, 0.268 mmol) and 2-chlorobenzyl bromide (55 mg, 0.268 mmol) in NMP (1 mL) was heated at 150° C. for 30 min under microwave irradiation. The reaction mixture was cooled to 25° C., diluted with EtOAc (15 mL), washed with water (2×10 mL), dried over anhydrous Na$_2$SO$_4$, filtered and evaporated under reduced pressure. The residue was purified by preparative HPLC [Xterra-RP18, 10μ, 19×250 mm/acetonitrile/10 mM using ammonium acetate in water as solvent system] to yield after evaporation of the product containing fractions the title compound (30 mg, 41%) as colorless sticky solid. MS (m/e): 405 (M+H).

Example 2

2-tert-butyl-7-[(2-chloro-4-fluorophenyl)methyl]-4-(3,3-difluoropyrrolidin-1-yl)pyrrolo[2,3-d]pyrimidine

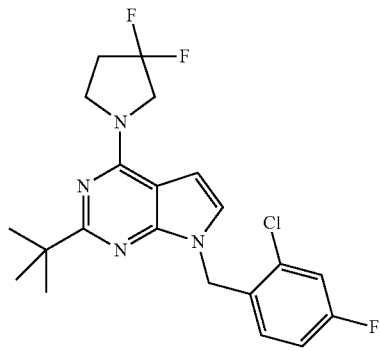 [SMILES: CC(C)(C)c1nc(N2CCC(F)(F)C2)c2ccn(Cc3ccc(F)cc3Cl)c2n1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 423 (M+H).

Example 3

2-tert-butyl-4-(3,3-difluoropyrrolidin-1-yl)-7-[(2-methylsulfonylphenyl)methyl]pyrrolo[2,3-d]pyrimidine

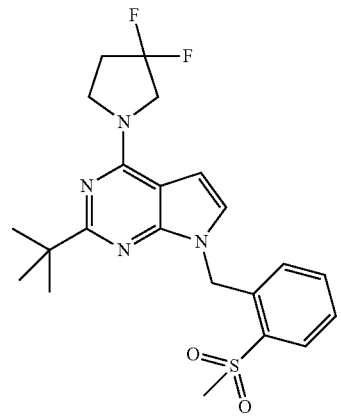 [SMILES: CC(C)(C)c1nc(N2CCC(F)(F)C2)c2ccn(Cc3ccccc3S(C)(=O)=O)c2n1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 449 (M+H).

Example 4

2-tert-butyl-4-(3,3-difluoropyrrolidin-1-yl)-7-[[2-(trifluoromethyl)phenyl]methyl]pyrrolo[2,3-d]pyrimidine

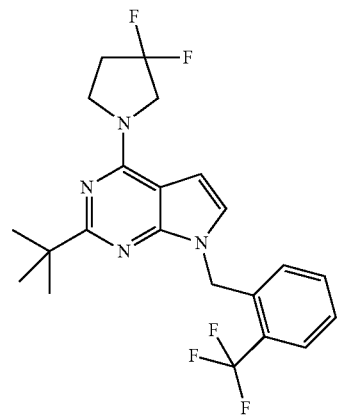 [SMILES: CC(C)(C)c1nc(N2CCC(F)(F)C2)c2ccn(Cc3ccccc3C(F)(F)F)c2n1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 439 (M+H).

Example 5

2-tert-butyl-7-[(2,3-dichlorophenyl)methyl]-4-(3,3-difluoropyrrolidin-1-yl) pyrrolo[2,3-d]pyrimidine

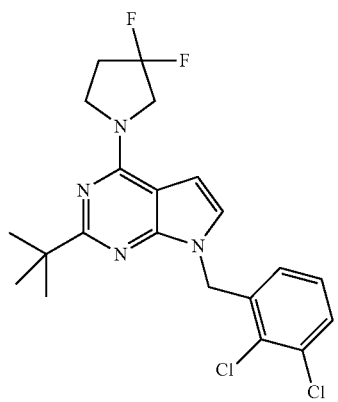 [SMILES: CC(C)(C)c1nc(N2CCC(F)(F)C2)c2ccn(Cc3cccc(Cl)c3Cl)c2n1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 439 (M+H).

Example 6

2-tert-butyl-7-[(2-chloropyridin-3-yl)methyl]-4-(3,3-difluoropyrrolidin-1-yl)pyrrolo[2,3-d]pyrimidine

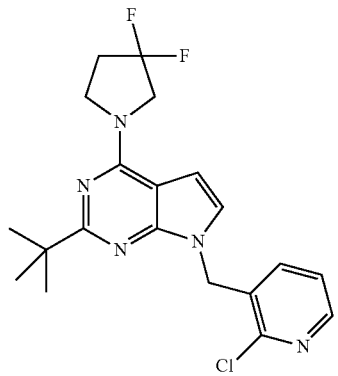 [SMILES: CC(C)(C)c1nc(N2CCC(F)(F)C2)c2ccn(Cc3cccnc3Cl)c2n1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 406 (M+H).

Example 7

2-tert-butyl-7-[(3-chloropyridin-2-yl)methyl]-4-(3,3-difluoropyrrolidin-1-yl)pyrrolo[2,3-d]pyrimidine

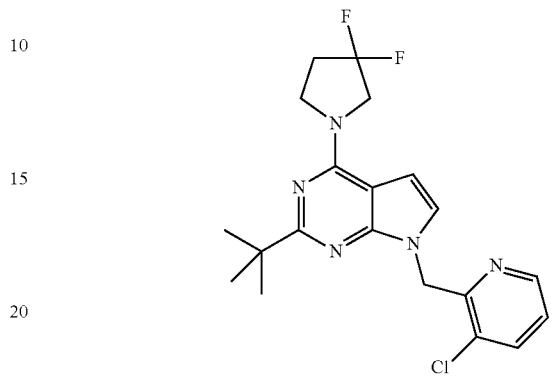

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 406 (M+H).

Example 8

5-[[2-tert-butyl-4-(3,3-difluoropyrrolidin-1-yl)pyrrolo[2,3-d]pyrimidin-7-yl]methyl]-3-methyl-1,2,4-oxadiazole

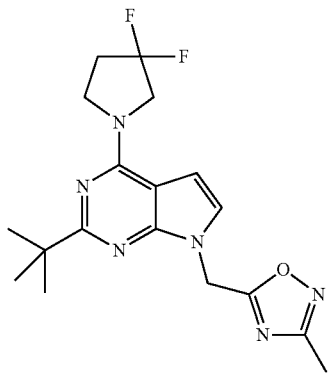 [SMILES: Cc1noc(Cn2ccc3c(N4CCC(F)(F)C4)nc(C(C)(C)C)nc32)n1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 377 (M+H).

Example 9

3-[[2-tert-butyl-4-(3,3-difluoropyrrolidin-1-yl)pyrrolo[2,3-d]pyrimidin-7-yl]methyl]-4-methyl-1,2,5-oxadiazole

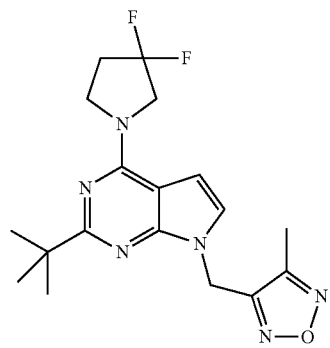 [SMILES: Cc1nonc1Cn1ccc2c(N3CCC(F)(F)C3)nc(C(C)(C)C)nc21]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 377 (M+H).

Example 10

2-[[2-tert-butyl-4-(3,3-difluoropyrrolidin-1-yl)pyrrolo[2,3-d]pyrimidin-7-yl]methyl]-5-methyl-1,3,4-oxadiazole

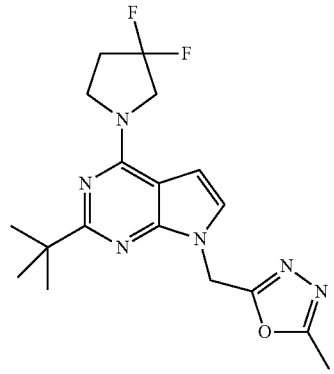 [SMILES: Cc1nnc(Cn2ccc3c(N4CCC(F)(F)C4)nc(C(C)(C)C)nc32)o1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 377 (M+H).

Example 11

2-tert-butyl-4-(3,3-difluoropyrrolidin-1-yl)-7-[(4,5-dimethyl-1,2,4-triazol-3-yl)methyl]pyrrolo[2,3-d]pyrimidine

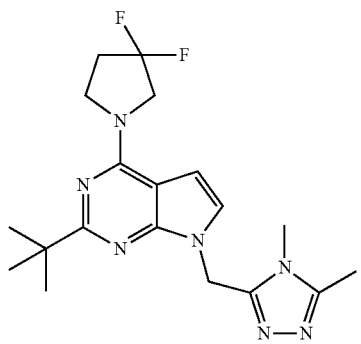 [SMILES: Cc1nnc(Cn2ccc3c(N4CCC(F)(F)C4)nc(C(C)(C)C)nc32)n1C]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 390 (M+H).

Example 12

2-tert-butyl-4-(3,3-difluoropyrrolidin-1-yl)-7-[(1-methyltetrazol-5-yl)methyl]pyrrolo[2,3-d]pyrimidine

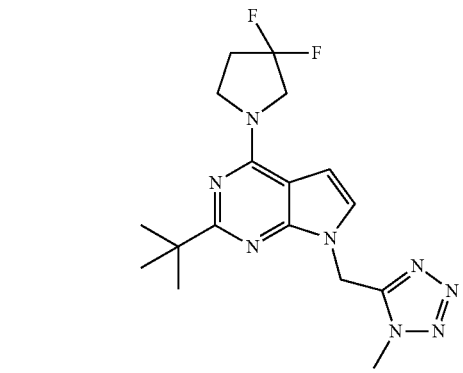 [SMILES: Cn1nnnc1Cn1ccc2c(N3CCC(F)(F)C3)nc(C(C)(C)C)nc21]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 377 (M+H).

Example 13

2-tert-butyl-7-[(1-cyclopropyltetrazol-5-yl)methyl]-4-(3,3-difluoropyrrolidin-1-yl)pyrrolo[2,3-d]pyrimidine

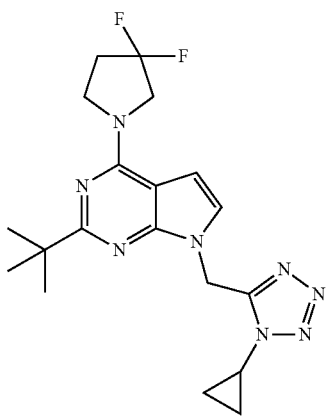 [SMILES: CC(C)(C)c1nc(N2CCC(F)(F)C2)c2ccn(Cc3nnnn3C3CC3)c2n1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 403 (M+H).

Example 14

6-[2-tert-butyl-7-[(2-chlorophenyl)methyl]pyrrolo[2,3-d]pyrimidin-4-yl]-2-oxa-6-azaspiro[3.3]heptane

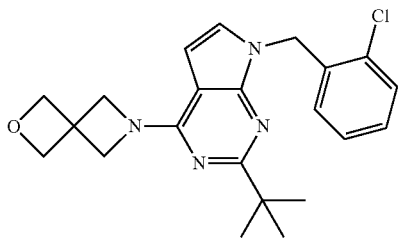 [SMILES: CC(C)(C)c1nc(N2CC3(COC3)C2)c2ccn(Cc3ccccc3Cl)c2n1]

a) 2-tert-Butyl-4-(2-oxa-6-aza-spiro[3.3]hept-6-yl)-7H-pyrrolo[2,3-d]pyrimidine

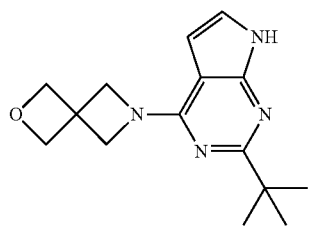 [SMILES: CC(C)(C)c1nc(N2CC3(COC3)C2)c2cc[nH]c2n1]

A solution of 2-tert-butyl-4-chloro-7H-pyrrolo[2,3-d]pyrimidine (1 g, 4.7 mmol), 2-oxa-6-aza-spiro[3.3]heptane oxalate salt (2 g, 7.18 mmol) and DIPEA (3 mL, 14.1 mmol) in EtOH (15 mL) was stirred in a sealed tube at 100° C. for 16 h. Volatilities were removed in vacuo and the residue was dissolved in DCM (20 mL). The organic layer was washed with water (2×10 mL) and brine (10 mL), dried over anhydrous Na$_2$SO$_4$, filtered, and evaporated. The residue was purified by column chromatography on silica eluting with 20% EtOAc/hexane to yield the title compound (750 mg, 57%) as white solid. MS (m/e): 273 (M+H).

b) 6-[2-tert-butyl-7-[(2-chlorophenyl)methyl]pyrrolo[2,3-d]pyrimidin-4-yl]-2-oxa-6-azaspiro[3.3]heptane A solution 2-tert-butyl-4-(2-oxa-6-aza-spiro[3.3]hept-6-yl)-7H-pyrrolo[2,3-d]pyrimidine (30 mg, 0.11 mmol), NaH (10 mg, 0.132 mmol) and bromomethyl-2-chloro-benzene (30 mg, 0.143 mmol) in DMF (5 mL) and stirred at 25° C. for 12 h. NH$_4$Cl aq. solution was added and concentrated in vacuo. The residue was dissolved in water (10 mL) and extracted with EtOAc (2×25 mL). Combined organic layer was washed with brine, dried over anhydrous Na$_2$SO$_4$, filtered and evaporated. The residue was purified by preparative HPLC to yield the title compound (14 mg, 32%) as off white sticky solid. MS (m/e): 397 (M+H).

Example 15

6-[2-tert-butyl-7-[(3-methyl-1,2,4-oxadiazol-5-yl)methyl]pyrrolo[2,3-d]pyrimidin-4-yl]-2-oxa-6-azaspiro[3.3]heptane

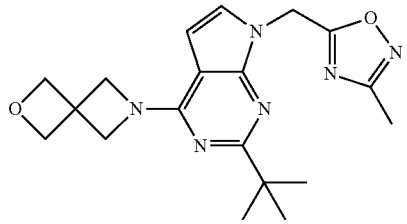 [SMILES: Cc1noc(Cn2ccc3c(N4CC5(COC5)C4)nc(C(C)(C)C)nc32)n1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 369 (M+H).

Example 16

6-[2-tert-butyl-7-[(3S)-oxolan-3-yl]pyrrolo[2,3-d]pyrimidin-4-yl]-2-oxa-6-azaspiro[3.3]heptane

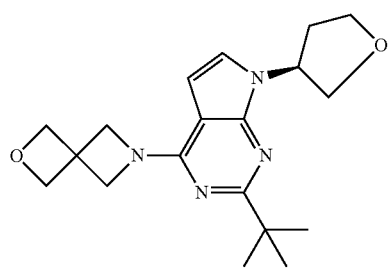 [SMILES: CC(C)(C)c1nc(N2CC3(COC3)C2)c2ccn([C@H]3CCOC3)c2n1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 343 (M+H).

Example 17

6-[2-tert-butyl-7-[(3R)-oxolan-3-yl]pyrrolo[2,3-d]pyrimidin-4-yl]-2-oxa-6-azaspiro[3.3]heptane

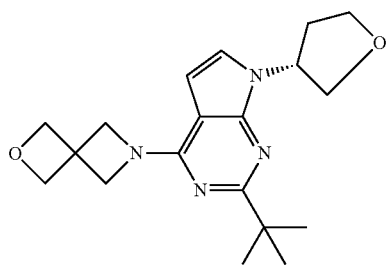 [SMILES: CC(C)(C)c1nc(N2CC3(COC3)C2)c2ccn([C@@H]3CCOC3)c2n1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 343 (M+H).

Example 18

6-[2-tert-butyl-7-[(2-chloro-4-fluorophenyl)methyl]pyrrolo[2,3-d]pyrimidin-4-yl]-2-oxa-6-azaspiro[3.3]heptane

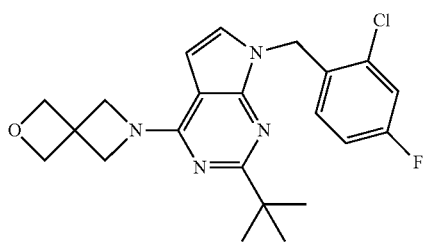 [SMILES: CC(C)(C)c1nc(N2CC3(COC3)C2)c2ccn(Cc3ccc(F)cc3Cl)c2n1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 415 (M+H).

Example 19

6-[2-tert-butyl-7-[(2-methylsulfonylphenyl)methyl]pyrrolo[2,3-d]pyrimidin-4-yl]-2-oxa-6-azaspiro[3.3]heptane

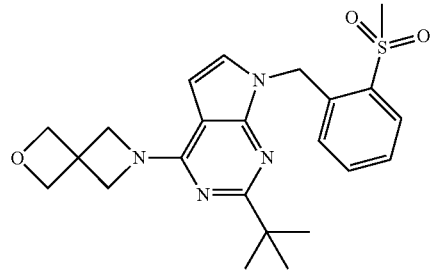 [SMILES: CC(C)(C)c1nc(N2CC3(COC3)C2)c2ccn(Cc3ccccc3S(C)(=O)=O)c2n1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 441 (M+H).

Example 20

6-[2-tert-butyl-7-[(2-chloropyridin-3-yl)methyl]pyrrolo[2,3-d]pyrimidin-4-yl]-2-oxa-6-azaspiro[3.3]heptane

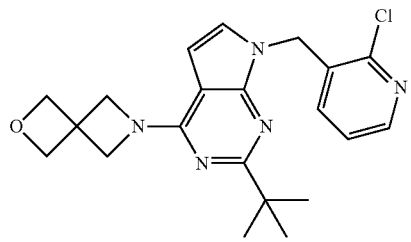 [SMILES: CC(C)(C)c1nc(N2CC3(COC3)C2)c2ccn(Cc3cccnc3Cl)c2n1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 398 (M+H).

Example 21

6-[2-tert-butyl-7-[(2,3-dichlorophenyl)methyl]pyrrolo[2,3-d]pyrimidin-4-yl]-2-oxa-6-azaspiro[3.3]heptane

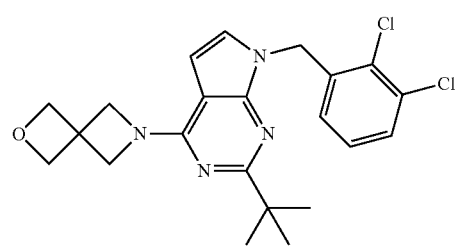 [SMILES: CC(C)(C)c1nc(N2CC3(COC3)C2)c2ccn(Cc3cccc(Cl)c3Cl)c2n1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 430.8 (M+H).

Example 22

6-[2-tert-butyl-7-[(4-methyl-1,2,5-oxadiazol-3-yl)methyl]pyrrolo[2,3-d]pyrimidin-4-yl]-2-oxa-6-azaspiro[3.3]heptane

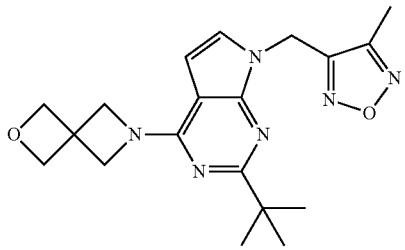 [SMILES: Cc1nonc1Cn1ccc2c(N3CC4(COC4)C3)nc(C(C)(C)C)nc21]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 369 (M+H).

Example 23

6-[2-tert-butyl-7-[(5-methyl-1,3,4-oxadiazol-2-yl)methyl]pyrrolo[2,3-d]pyrimidin-4-yl]-2-oxa-6-azaspiro[3.3]heptane

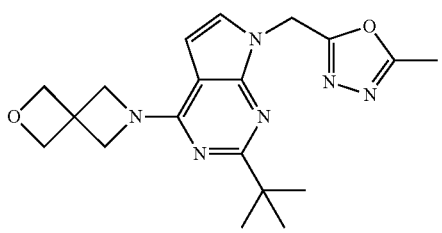 [SMILES: Cc1nnc(Cn2ccc3c(N4CC5(COC5)C4)nc(C(C)(C)C)nc32)o1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 369.6 (M+H).

Example 24

1-[2-tert-butyl-7-[(2-chlorophenyl)methyl]pyrrolo[2,3-d]pyrimidin-4-yl]pyrrolidin-3-ol

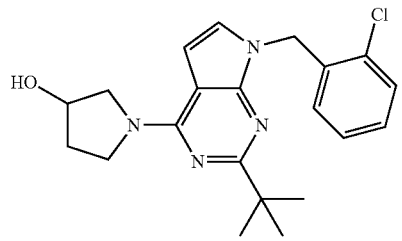 [SMILES: CC(C)(C)c1nc(N2CCC(O)C2)c2ccn(Cc3ccccc3Cl)c2n1]

a) Acetic acid 1-(2-tert-butyl-7H-pyrrolo[2,3-d]pyrimidin-4-yl)-pyrrolidin-3-yl ester

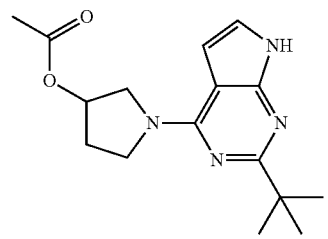 [SMILES: CC(=O)OC1CCN(c2nc(C(C)(C)C)nc3[nH]ccc23)C1]

In analogy to the procedure described for the synthesis of 2-tert-Butyl-4-(3,3-difluoro-pyrrolidin-1-yl)-7H-pyrrolo[2,3-d]pyrimidine (example 1, step c) the title compound was prepared from 2-tert-butyl-4-chloro-7H-pyrrolo[2,3-d]pyrimidine and acetic acid pyrrolidin-3-yl ester. MS (m/e): 303 (M+H).

b) 1-[2-tert-butyl-7-[(2-chlorophenyl)methyl]pyrrolo[2,3-d]pyrimidin-4-yl]pyrrolidin-3-ol To a solution of acetic acid 1-(2-tert-butyl-7H-pyrrolo[2,3-d]pyrimidin-4-yl)-pyrrolidin-3-yl ester (100 mg, 0.33 mmol) in dry DMF (5 mL) was added NaH (60% in oil; 40 mg; 0.99 mmol) at 0° C. and the reaction mixture was stirred at 25° C. for 1 h. 1-bromomethyl-2-chloro-benzene (135.3 mg, 0.66 mmol) was added at 0° C. and the reaction mixture was stirred at 25° C. for 12 h. The mixture was quenched with aqueous $NH_4Cl$ solution (10 mL) and extracted with EtOAc (2×20 mL). The combined organic layer was washed with water (10 mL), dried over anhydrous $Na_2SO_4$, filtered and evaporated. The residue was purified by preparative HPLC [Xterra-RP18, 10μ, 19×250 mm/acetonitrile/10 mM using ammonium acetate in water as solvent system] to yield the title compound (60 mg, 46%) as colorless sticky solid. MS (m/e): 385 (M+H).

Example 25

1-[2-tert-butyl-7-[(2-chloro-4-fluorophenyl)methyl]pyrrolo[2,3-d]pyrimidin-4-yl]pyrrolidin-3-ol

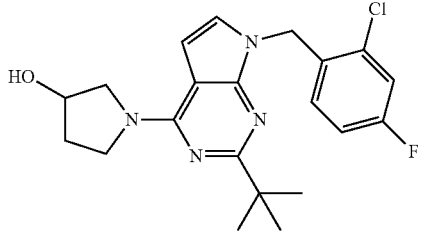 [SMILES: CC(C)(C)c1nc(N2CCC(O)C2)c2ccn(Cc3ccc(F)cc3Cl)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 403 (M+H).

Example 26

1-[2-tert-butyl-7-[(2-methylsulfonylphenyl)methyl]pyrrolo[2,3-d]pyrimidin-4-yl]pyrrolidin-3-ol

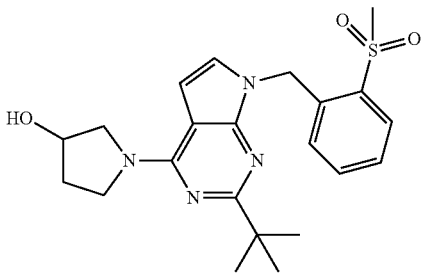 [SMILES: CC(C)(C)c1nc(N2CCC(O)C2)c2ccn(Cc3ccccc3S(C)(=O)=O)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 429 (M+H).

Example 27

1-[2-tert-butyl-7-[[2-(trifluoromethyl)phenyl]methyl]pyrrolo[2,3-d]pyrimidin-4-yl]pyrrolidin-3-ol

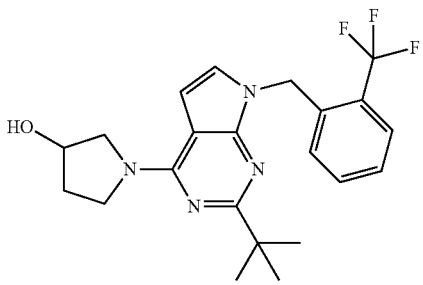 [SMILES: CC(C)(C)c1nc(N2CCC(O)C2)c2ccn(Cc3ccccc3C(F)(F)F)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 419 (M+H).

Example 28

1-[2-tert-butyl-7-[(2,3-dichlorophenyl)methyl]pyrrolo[2,3-d]pyrimidin-4-yl]pyrrolidin-3-ol

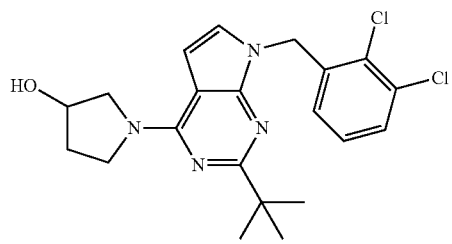 [SMILES: CC(C)(C)c1nc(N2CCC(O)C2)c2ccn(Cc3cccc(Cl)c3Cl)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 419 (M+H).

Example 29

1-[2-tert-butyl-7-[(2-chloropyridin-3-yl)methyl]pyrrolo[2,3-d]pyrimidin-4-yl]pyrrolidin-3-ol

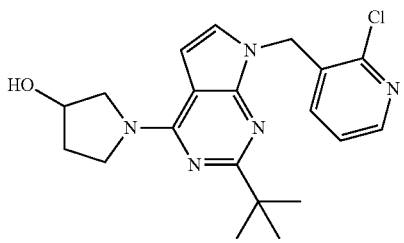 [SMILES: CC(C)(C)c1nc(N2CCC(O)C2)c2ccn(Cc3cccnc3Cl)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 386 (M+H).

Example 30

1-[2-tert-butyl-7-[(3-chloropyridin-2-yl)methyl]pyrrolo[2,3-d]pyrimidin-4-yl]pyrrolidin-3-ol

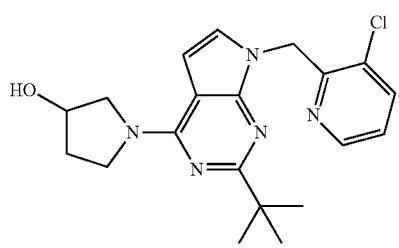

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 386 (M+H).

Example 31

1-[2-tert-butyl-7-[(3-methyl-1,2,4-oxadiazol-5-yl)methyl]pyrrolo[2,3-d]pyrimidin-4-yl]pyrrolidin-3-ol

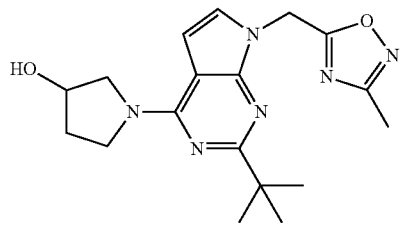 [SMILES: Cc1noc(Cn2ccc3c(N4CCC(O)C4)nc(C(C)(C)C)nc32)n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 357 (M+H).

Example 32

1-[2-tert-butyl-7-[(4-methyl-1,2,5-oxadiazol-3-yl)methyl]pyrrolo[2,3-d]pyrimidin-4-yl]pyrrolidin-3-ol

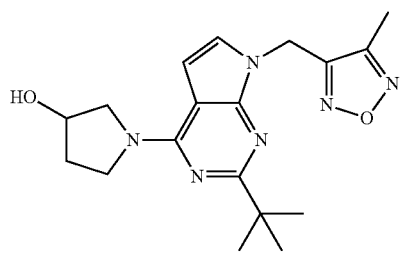 [SMILES: Cc1nonc1Cn1ccc2c(N3CCC(O)C3)nc(C(C)(C)C)nc21]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 357 (M+H).

Example 33

1-[2-tert-butyl-7-[(5-methyl-1,3,4-oxadiazol-2-yl)methyl]pyrrolo[2,3-d]pyrimidin-4-yl]pyrrolidin-3-ol

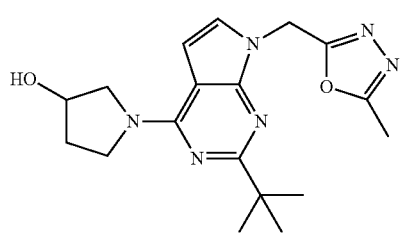 [SMILES: Cc1nnc(Cn2ccc3c(N4CCC(O)C4)nc(C(C)(C)C)nc32)o1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 357 (M+H).

Example 34

1-[2-tert-butyl-7-[(1-methyltetrazol-5-yl)methyl]pyrrolo[2,3-d]pyrimidin-4-yl]pyrrolidin-3-ol

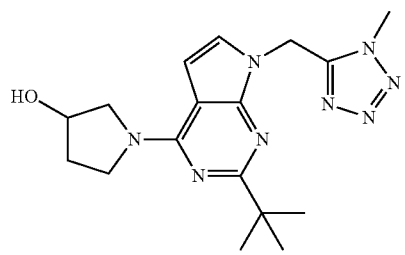 [SMILES: Cn1nnnc1Cn1ccc2c(N3CCC(O)C3)nc(C(C)(C)C)nc21]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 357 (M+H).

Example 35

[1-[2-tert-butyl-7-[(1-methyltetrazol-5-yl)methyl]pyrrolo[2,3-d]pyrimidin-4-yl]pyrrolidin-3-yl]acetate

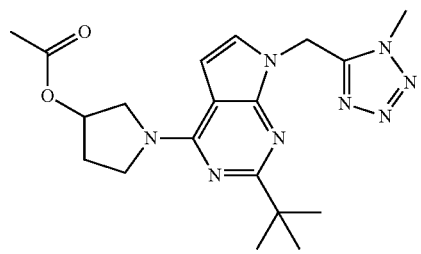 [SMILES: CC(=O)OC1CCN(c2nc(C(C)(C)C)nc3c2ccn3Cc2nnnn2C)C1]

To a solution of acetic acid 1-(2-tert-butyl-7H-pyrrolo[2,3-d]pyrimidin-4-yl)-pyrrolidin-3-yl ester (example 24, step a) (50 mg, 0.16 mmol) in dry DMF (5 mL) was added NaH (60% in oil; 10 mg; 0.192 mmol) at 0° C. and the reaction mixture was stirred at 25° C. for 1 h. To this solution was then added 5-chloromethyl-1-methyl-1H-tetrazole (28 mg, 0.20 mmol) at 0° C. and the reaction mixture was stirred at 25° C. for 12 h. The mixture was quenched with aqueous $NH_4Cl$ solution (10 mL) and extracted with EtOAc (2×10 mL). The combined organic layer were washed with water (10 mL), dried over anhydrous $Na_2SO_4$, filtered and evaporated. The residue was purified by preparative HPLC [Xterra-RP18, 10μ, 19×250 mm/acetonitrile/10 mM using ammonium acetate in water as solvent system] to yield the title compound (32 mg, 48%) as off white solid. MS (m/e): 399.2 (M+H).

Example 36

[1-[2-tert-butyl-7-[(2,3-dichlorophenyl)methyl]pyrrolo[2,3-d]pyrimidin-4-yl]pyrrolidin-3-yl]acetate

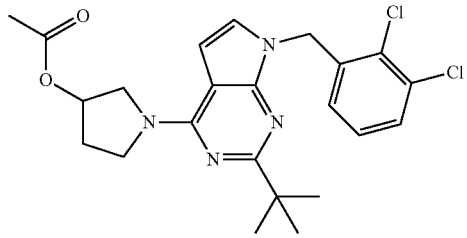 [SMILES: CC(=O)OC1CCN(c2nc(C(C)(C)C)nc3c2ccn3Cc2cccc(Cl)c2Cl)C1]

In analogy to the procedure described for the synthesis of [1-[2-tert-butyl-7-[(1-methyltetrazol-5-yl)methyl]pyrrolo[2,3-d]pyrimidin-4-yl]pyrrolidin-3-yl]acetate (example 35) the title compound was prepared from acetic acid 1-(2-tert-butyl-7H-pyrrolo[2,3-d]pyrimidin-4-yl)-pyrrolidin-3-yl ester and 1-bromomethyl-2,3-dichloro-benzene. MS (m/e): 460.8 (M+H).

Example 37

[1-[2-tert-butyl-7-[(4-methyl-1,2,5-oxadiazol-3-yl)methyl]pyrrolo[2,3-d]pyrimidin-4-yl]pyrrolidin-3-yl]acetate

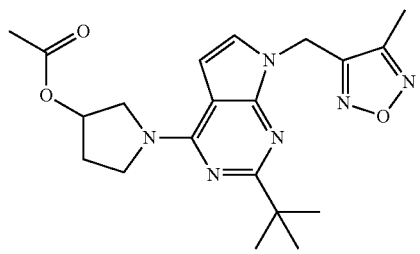 [SMILES: CC(=O)OC1CCN(c2nc(C(C)(C)C)nc3c2ccn3Cc2nonc2C)C1]

In analogy to the procedure described for the synthesis of [1-[2-tert-butyl-7-[(1-methyltetrazol-5-yl)methyl]pyrrolo[2,3-d]pyrimidin-4-yl]pyrrolidin-3-yl]acetate (example 35) the title compound was prepared from acetic acid 1-(2-tert-butyl-7H-pyrrolo[2,3-d]pyrimidin-4-yl)-pyrrolidin-3-yl ester and 3-chloromethyl-4-methyl-furazan. MS (m/e): 399 (M+H).

Example 38

1-[2-tert-butyl-7-[(1-cyclopropyltetrazol-5-yl)methyl]pyrrolo[2,3-d]pyrimidin-4-yl]pyrrolidin-3-ol

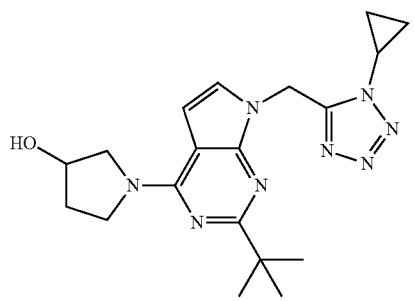 [SMILES: CC(C)(C)c1nc(N2CCC(O)C2)c2ccn(Cc3nnnn3C3CC3)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 383 (M+H).

Example 39

1-[2-tert-butyl-7-[(3R)-oxolan-3-yl]pyrrolo[2,3-d]pyrimidin-4-yl]pyrrolidin-3-ol

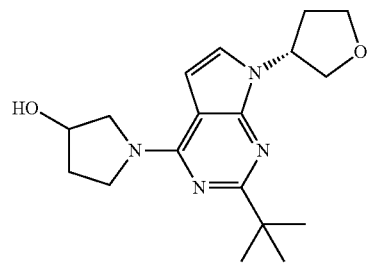 [SMILES: CC(C)(C)c1nc(N2CCC(O)C2)c2ccn([C@@H]3CCOC3)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 331.2 (M+H).

Example 40

1-[2-tert-butyl-7-[[3-(trifluoromethyl)-1H-pyrazol-4-yl]methyl]pyrrolo[2,3-d]pyrimidin-4-yl]pyrrolidin-3-ol

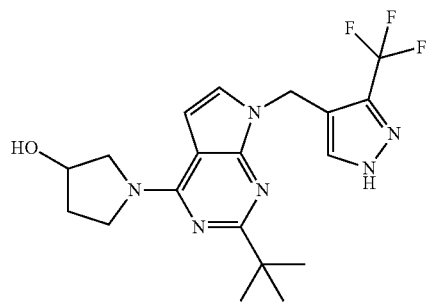 [SMILES: CC(C)(C)c1nc(N2CCC(O)C2)c2ccn(Cc3c[nH]nc3C(F)(F)F)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid 1-(2-tert-butyl-7H-pyrrolo[2,3-d]pyrimidin-4-yl)-pyrrolidin-3-yl ester (example 24, step a). MS (m/e): 409.2 (M+H).

Example 41

2-tert-butyl-4-(3,3-difluoropyrrolidin-1-yl)-7-[[3-(trifluoromethyl)-1H-pyrazol-4-yl]methyl]pyrrolo[2,3-d]pyrimidine

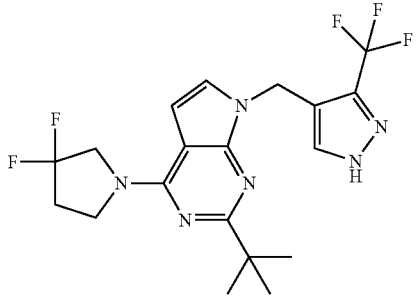 [SMILES: CC(C)(C)c1nc(N2CCC(F)(F)C2)c2ccn(Cc3c[nH]nc3C(F)(F)F)c2n1]

In analogy to the procedure described for the synthesis of 2-tert-butyl-7-[(2-chlorophenyl)methyl]-4-(3,3-difluoropyrrolidin-1-yl)pyrrolo[2,3-d]pyrimidine (example 1) the title compound was prepared from 2-tert-butyl-4-(3,3-difluoropyrrolidin-1-yl)-7H-pyrrolo[2,3-d]pyrimidine (example 1, step c). MS (m/e): 428.8 (M+H).

Example 42

(3S)-1-[2-tert-butyl-7-[(2,3-dichlorophenyl)methyl]pyrrolo[2,3-d]pyrimidin-4-yl]pyrrolidin-3-ol

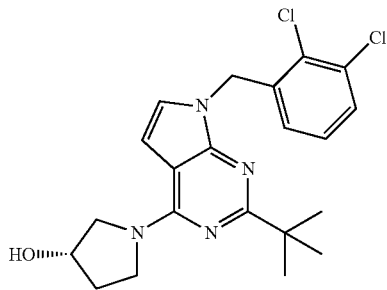 [SMILES: CC(C)(C)c1nc(N2CC[C@H](O)C2)c2ccn(Cc3cccc(Cl)c3Cl)c2n1]

Preparative HPLC-separation on reprosil Chiral NR of 1-[2-tert-butyl-7-[(2,3-dichlorophenyl)methyl]pyrrolo[2,3-d]pyrimidin-4-yl]pyrrolidin-3-ol (example 28) yielded the title compound as white foam. MS (m/e): 419.1 (M+H).

Example 43

(3S)-1-[2-tert-butyl-7-[(2-chloro-4-fluorophenyl)methyl]pyrrolo[2,3-d]pyrimidin-4-yl]pyrrolidin-3-ol

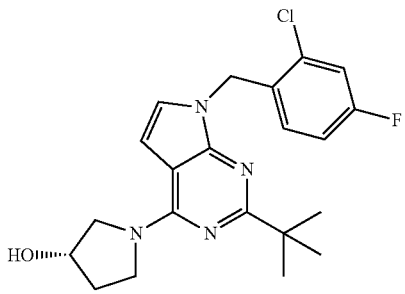 [SMILES: CC(C)(C)c1nc(N2CC[C@H](O)C2)c2ccn(Cc3ccc(F)cc3Cl)c2n1]

Preparative HPLC-separation on reprosil Chiral NR of 1-[2-tert-butyl-7-[(2-chloro-4-fluorophenyl)methyl]pyrrolo[2,3-d]pyrimidin-4-yl]pyrrolidin-3-ol (example 25) yielded the title compound as colorless foam. MS (m/e): 403.1 (M+H).

Example 44

(3S)-1-[2-tert-butyl-7-[[2-(trifluoromethyl)phenyl]methyl]pyrrolo[2,3-d]pyrimidin-4-yl]pyrrolidin-3-ol

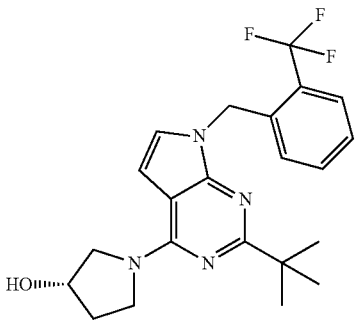 [SMILES: CC(C)(C)c1nc(N2CC[C@H](O)C2)c2ccn(Cc3ccccc3C(F)(F)F)c2n1]

Preparative HPLC-separation on reprosil Chiral NR of 1-[2-tert-butyl-7-[[2-(trifluoromethyl)phenyl]methyl]pyrrolo[2,3-d]pyrimidin-4-yl]pyrrolidin-3-ol (example 27) yielded the title compound as white foam. MS (m/e): 419.2 (M+H).

Example 45

(3S)-1-[2-tert-butyl-7-[(2-methylsulfonylphenyl)methyl]pyrrolo[2,3-d]pyrimidin-4-yl]pyrrolidin-3-ol

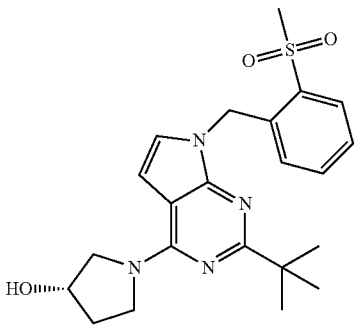 [SMILES: CC(C)(C)c1nc(N2CC[C@H](O)C2)c2ccn(Cc3ccccc3S(C)(=O)=O)c2n1]

Preparative HPLC-separation on reprosil Chiral NR of 1-[2-tert-butyl-7-[(2-methylsulfonylphenyl)methyl]pyrrolo[2,3-d]pyrimidin-4-yl]pyrrolidin-3-ol (example 26) yielded the title compound as white foam. MS (m/e): 429.2 (M+H).

Example 46

(3S)-1-[2-tert-butyl-7-[(2-chloropyridin-3-yl)methyl]pyrrolo[2,3-d]pyrimidin-4-yl]pyrrolidin-3-ol

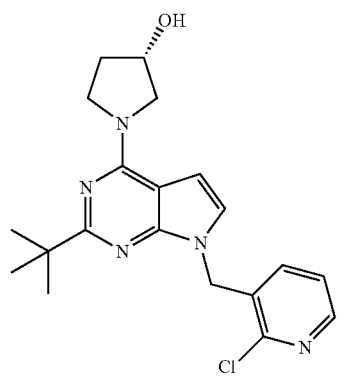 [SMILES: CC(C)(C)c1nc(N2CC[C@H](O)C2)c2ccn(Cc3cccnc3Cl)c2n1]

a) Acetic acid (S)-1-(2-tert-butyl-7H-pyrrolo[2,3-d]pyrimidin-4-yl)-pyrrolidin-3-yl ester

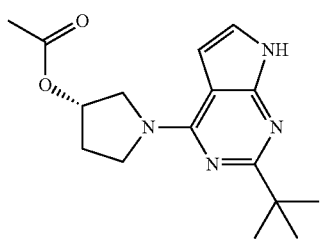

In analogy to the procedure described for the synthesis of 2-tert-Butyl-4-(3,3-difluoro-pyrrolidin-1-yl)-7H-pyrrolo[2,3-d]pyrimidine (example 1, step c) the title compound was prepared from 2-tert-butyl-4-chloro-7H-pyrrolo[2,3-d]pyrimidine and acetic acid pyrrolidin-3-yl ester. MS (m/e): 303 (M+H).

b) (3S)-1-[2-tert-butyl-7-[(2-chloropyridin-3-yl)methyl]pyrrolo[2,3-d]pyrimidin-4-yl]pyrrolidin-3-ol In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid (S)-1-(2-tert-butyl-7H-pyrrolo[2,3-d]pyrimidin-4-yl)-pyrrolidin-3-yl ester (example 46, step a). MS (m/e): 386 (M+H).

Example 47

(3S)-1-[2-tert-butyl-7-[(3-chloropyridin-2-yl)methyl]pyrrolo[2,3-d]pyrimidin-4-yl]pyrrolidin-3-ol

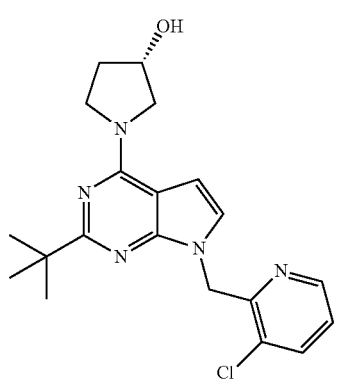 [SMILES: CC(C)(C)c1nc(N2CC[C@H](O)C2)c2ccn(Cc3ncccc3Cl)c2n1]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid (S)-1-(2-tert-butyl-7H-pyrrolo[2,3-d]pyrimidin-4-yl)-pyrrolidin-3-yl ester (example 46, step a). MS (m/e): 386 (M+H).

Example 48

(3S)-1-[2-tert-butyl-7-[(4-methyl-1,2,5-oxadiazol-3-yl)methyl]pyrrolo[2,3-d]pyrimidin-4-yl]pyrrolidin-3-ol

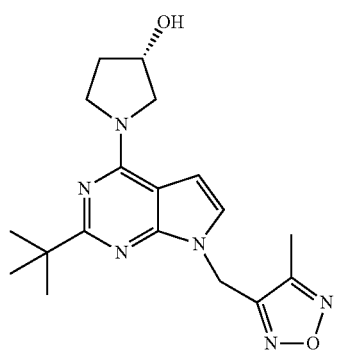 [SMILES: Cc1nonc1Cn1ccc2c(N3CC[C@H](O)C3)nc(C(C)(C)C)nc21]

In analogy to the procedure described for the synthesis of 1-[2-tert-butyl-7-[(2-chlorophenyl)methyl]pyrrolo[2,3-d]pyrimidin-4-yl]pyrrolidin-3-ol (example 24) the title compound was prepared from acetic acid (S)-1-(2-tert-butyl-7H-pyrrolo[2,3-d]pyrimidin-4-yl)-pyrrolidin-3-yl ester (example 46, step a). MS (m/e): 357.2 (M+H).

Example 49

6-[2-tert-butyl-7-[(3-chloropyridin-2-yl)methyl]pyrrolo[2,3-d]pyrimidin-4-yl]-2-oxa-6-azaspiro[3.3]heptane

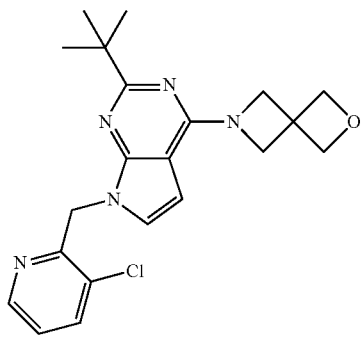 [SMILES: CC(C)(C)c1nc(N2CC3(COC3)C2)c2ccn(Cc3ncccc3Cl)c2n1]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 398 (M+H).

Example 50

6-[2-tert-butyl-7-[(1-methyltetrazol-5-yl)methyl]pyrrolo[2,3-d]pyrimidin-4-yl]-2-oxa-6-azaspiro[3.3]heptane

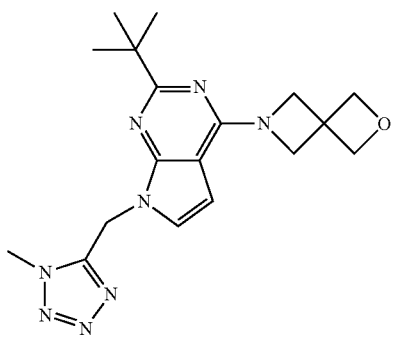 [SMILES: Cn1nnnc1Cn1ccc2c(N3CC4(COC4)C3)nc(C(C)(C)C)nc21]

In analogy to the procedure described for the synthesis of 6-[2-tert-butyl-7-[(2-chlorophenyl)methyl]pyrrolo[2,3-d]pyrimidin-4-yl]-2-oxa-6-azaspiro[3.3]heptane (example 14) the title compound was prepared from 2-tert-Butyl-4-(2-oxa-6-aza-spiro[3.3]hept-6-yl)-7H-pyrrolo[2,3-d]pyrimidine (example 14, step a). MS (m/e): 369 (M+H).

Example 51

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 µM, more particularly of 1 nM to 3 µM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1x HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

The compounds of the invention are CB2 receptor agonists with $EC_{50}$ below 1 µM and selectivity versus CB1 in the corresponding assay of at least 10 fold. Particular compound of the invention are CB2 receptor agonists with $EC_{50}$ below 0.05 µM and selectivity versus CB1 in the corresponding assay of at least 500 fold.

For example, the following compounds showed the following human $EC_{50}$ values in the functional cAMP assay described above:

| Example | EC50:CB2 | Ec50:CB1 |
|---|---|---|
| 1 | 0.0101 | >10 |
| 2 | 0.0265 | >10 |
| 3 | 0.0116 | >10 |
| 4 | 0.0074 | >10 |
| 5 | 0.0125 | >10 |
| 6 | 0.012 | >10 |
| 7 | 0.0042 | >10 |
| 8 | 0.0496 | >10 |
| 9 | 0.0095 | >10 |
| 10 | 0.0296 | >10 |
| 11 | 0.0308 | >10 |
| 12 | 0.014 | >10 |
| 13 | 0.023 | >10 |
| 14 | 0.0153 | >10 |
| 15 | 0.7473 | >10 |
| 16 | 0.0787 | >10 |
| 17 | 0.0618 | >10 |
| 18 | 0.0425 | >10 |
| 19 | 0.0146 | >10 |
| 20 | 0.0242 | >10 |
| 21 | 0.0914 | >10 |
| 22 | 0.0484 | >10 |
| 23 | 0.4682 | >10 |
| 24 | 0.4114 | >10 |
| 25 | 0.0102 | 0.8953 |
| 26 | 0.0168 | >10 |
| 27 | 0.0069 | >10 |
| 28 | 0.014 | >10 |
| 29 | 0.0036 | >10 |
| 30 | 0.0084 | >10 |
| 31 | 0.3157 | >10 |
| 32 | 0.0189 | >10 |
| 33 | 0.3498 | >10 |
| 34 | 0.1344 | >10 |
| 35 | 0.2775 | >10 |
| 36 | 0.0853 | >10 |
| 37 | 0.0887 | >10 |
| 38 | 0.1727 | >10 |
| 39 | 0.035 | >10 |
| 40 | 0.0356 | >10 |
| 41 | 0.0135 | 1.8447 |
| 42 | 0.0035 | >10 |
| 43 | 0.0063 | >10 |
| 44 | 0.0033 | >10 |
| 45 | 0.0042 | >10 |
| 46 | 0.0051 | >10 |
| 47 | 0.0058 | >10 |
| 48 | 0.0085 | >10 |
| 49 | 0.0107 | 0.3068 |
| 50 | 0.5313 | >10 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

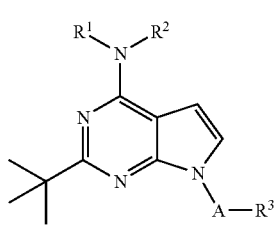

wherein

A is $CH_2$ or absent;

$R^1$ and $R^2$, together with the nitrogen atom to which they are attached form substituted pyrrolidinyl or 2-oxa-6-azaspiro[3.3]heptyl, wherein substituted pyrrolidinyl is pyrrolidinyl substituted with one or two substituents independently selected from halogen, hydroxyl and alkylcarbonyloxy; and $R^3$ is halophenyl, alkylsulfonylphenyl, haloalkylphenyl, halopyridinyl, alkyloxadiazolyl, alkyltriazolyl, alkyltetrazolyl, oxolanyl, cycloalkyltetrazolyl or haloalkyl-1H-pyrazolyl;

or a pharmaceutically acceptable salt or ester thereof.

2. A compound according to claim 1, wherein A is $CH_2$.

3. A compound according to claim 1, wherein $R^1$ and $R^2$, together with the nitrogen atom to which they are attached form substituted pyrrolidinyl, wherein substituted pyrrolidinyl is pyrrolidinyl substituted with one or two substituents independently selected from halogen and hydroxyl.

4. A compound according to claim 1, wherein $R^1$ and $R^2$, together with the nitrogen atom to which they are attached form substituted pyrrolidinyl, wherein substituted pyrrolidinyl is pyrrolidinyl substituted with one or two substituents independently selected from fluorine and hydroxyl.

5. A compound according to claim 1, wherein $R^1$ and $R^2$, together with the nitrogen atom to which they are attached form difluoropyrrolidinyl or hydroxypyrrolidinyl.

6. A compound according to claim 1, wherein $R^3$ is halophenyl, haloalkylphenyl, alkylsulfonylphenyl, halopyridinyl or alkyloxadiazolyl.

7. A compound according to claim 1, wherein $R^3$ is dichlorophenyl, chlorofluorophenyl, trifluoromethylphenyl, methylsulfonylphenyl, chloropyridinyl or methyloxadiazolyl.

8. A compound according to claim 1 selected from
2-tert-butyl-7-[(2-chlorophenyl)methyl]-4-(3,3-difluoropyrrolidin-1-yl)pyrrolo[2,3-d]pyrimidine;
2-tert-butyl-7-[(2-chloro-4-fluorophenyl)methyl]-4-(3,3-difluoropyrrolidin-1-yl)pyrrolo[2,3-d]pyrimidine;
2-tert-butyl-4-(3,3-difluoropyrrolidin-1-yl)-7-[(2-methylsulfonylphenyl)methyl]pyrrolo[2,3-d]pyrimidine;
2-tert-butyl-4-(3,3-difluoropyrrolidin-1-yl)-7-[[2-(trifluoromethyl)phenyl]methyl]pyrrolo[2,3-d]pyrimidine;
2-tert-butyl-7-[(2,3-dichlorophenyl)methyl]-4-(3,3-difluoropyrrolidin-1-yl)pyrrolo[2,3-d]pyrimidine;
2-tert-butyl-7-[(2-chloropyridin-3-yl)methyl]-4-(3,3-difluoropyrrolidin-1-yl)pyrrolo[2,3-d]pyrimidine;
2-tert-butyl-7-[(3-chloropyridin-2-yl)methyl]-4-(3,3-difluoropyrrolidin-1-yl)pyrrolo[2,3-d]pyrimidine;
5-[[2-tert-butyl-4-(3,3-difluoropyrrolidin-1-yl)pyrrolo[2,3-d]pyrimidin-7-yl]methyl]-3-methyl-1,2,4-oxadiazole;
3-[[2-tert-butyl-4-(3,3-difluoropyrrolidin-1-yl)pyrrolo[2,3-d]pyrimidin-7-yl]methyl]-4-methyl-1,2,5-oxadiazole;
2-[[2-tert-butyl-4-(3,3-difluoropyrrolidin-1-yl)pyrrolo[2,3-d]pyrimidin-7-yl]methyl]-5-methyl-1,3,4-oxadiazole;
2-tert-butyl-4-(3,3-difluoropyrrolidin-1-yl)-7-[(4,5-dimethyl-1,2,4-triazol-3-yl)methyl]pyrrolo[2,3-d]pyrimidine;
2-tert-butyl-4-(3,3-difluoropyrrolidin-1-yl)-7-[(1-methyltetrazol-5-yl)methyl]pyrrolo[2,3-d]pyrimidine;
2-tert-butyl-7-[(1-cyclopropyltetrazol-5-yl)methyl]-4-(3,3-difluoropyrrolidin-1-yl)pyrrolo[2,3-d]pyrimidine;
6-[2-tert-butyl-7-[(2-chlorophenyl)methyl]pyrrolo[2,3-d]pyrimidin-4-yl]-2-oxa-6-azaspiro[3.3]heptane;
6-[2-tert-butyl-7-[(3-methyl-1,2,4-oxadiazol-5-yl)methyl]pyrrolo[2,3-d]pyrimidin-4-yl]-2-oxa-6-azaspiro[3.3]heptane;
6-[2-tert-butyl-7-[(3S)-oxolan-3-yl]pyrrolo[2,3-d]pyrimidin-4-yl]-2-oxa-6-azaspiro[3.3]heptane;
6-[2-tert-butyl-7-[(3R)-oxolan-3-yl]pyrrolo[2,3-d]pyrimidin-4-yl]-2-oxa-6-azaspiro[3.3]heptane;
6-[2-tert-butyl-7-[(2-chloro-4-fluorophenyl)methyl]pyrrolo[2,3-d]pyrimidin-4-yl]-2-oxa-6-azaspiro[3.3]heptane;
6-[2-tert-butyl-7-[(2-methylsulfonylphenyl)methyl]pyrrolo[2,3-d]pyrimidin-4-yl]-2-oxa-6-azaspiro[3.3]heptane;
6-[2-tert-butyl-7-[(2-chloropyridin-3-yl)methyl]pyrrolo[2,3-d]pyrimidin-4-yl]-2-oxa-6-azaspiro[3.3]heptane;
6-[2-tert-butyl-7-[(2,3-dichlorophenyl)methyl]pyrrolo[2,3-d]pyrimidin-4-yl]-2-oxa-6-azaspiro[3.3]heptane;
6-[2-tert-butyl-7-[(4-methyl-1,2,5-oxadiazol-3-yl)methyl]pyrrolo[2,3-d]pyrimidin-4-yl]-2-oxa-6-azaspiro[3.3]heptane;
6-[2-tert-butyl-7-[(5-methyl-1,3,4-oxadiazol-2-yl)methyl]pyrrolo[2,3-d]pyrimidin-4-yl]-2-oxa-6-azaspiro[3.3]heptane;
1-[2-tert-butyl-7-[(2-chlorophenyl)methyl]pyrrolo[2,3-d]pyrimidin-4-yl]pyrrolidin-3-ol;
1-[2-tert-butyl-7-[(2-chloro-4-fluorophenyl)methyl]pyrrolo[2,3-d]pyrimidin-4-yl]pyrrolidin-3-ol;
1-[2-tert-butyl-7-[(2-methylsulfonylphenyl)methyl]pyrrolo[2,3-d]pyrimidin-4-yl]pyrrolidin-3-ol;
1-[2-tert-butyl-7-[[2-(trifluoromethyl)phenyl]methyl]pyrrolo[2,3-d]pyrimidin-4-yl]pyrrolidin-3-ol;
1-[2-tert-butyl-7-[(2,3-dichlorophenyl)methyl]pyrrolo[2,3-d]pyrimidin-4-yl]pyrrolidin-3-ol;
1-[2-tert-butyl-7-[(2-chloropyridin-3-yl)methyl]pyrrolo[2,3-d]pyrimidin-4-yl]pyrrolidin-3-ol;
1-[2-tert-butyl-7-[(3-chloropyridin-2-yl)methyl]pyrrolo[2,3-d]pyrimidin-4-yl]pyrrolidin-3-ol;
1-[2-tert-butyl-7-[(3-methyl-1,2,4-oxadiazol-5-yl)methyl]pyrrolo[2,3-d]pyrimidin-4-yl]pyrrolidin-3-ol;
1-[2-tert-butyl-7-[(4-methyl-1,2,5-oxadiazol-3-yl)methyl]pyrrolo[2,3-d]pyrimidin-4-yl]pyrrolidin-3-ol;
1-[2-tert-butyl-7-[(5-methyl-1,3,4-oxadiazol-2-yl)methyl]pyrrolo[2,3-d]pyrimidin-4-yl]pyrrolidin-3-ol;
1-[2-tert-butyl-7-[(1-methyltetrazol-5-yl)methyl]pyrrolo[2,3-d]pyrimidin-4-yl]pyrrolidin-3-ol;
[1-[2-tert-butyl-7-[(1-methyltetrazol-5-yl)methyl]pyrrolo[2,3-d]pyrimidin-4-yl]pyrrolidin-3-yl]acetate;
[1-[2-tert-butyl-7-[(2,3-dichlorophenyl)methyl]pyrrolo[2,3-d]pyrimidin-4-yl]pyrrolidin-3-yl]acetate;
[1-[2-tert-butyl-7-[(4-methyl-1,2,5-oxadiazol-3-yl)methyl]pyrrolo[2,3-d]pyrimidin-4-yl]pyrrolidin-3-yl]acetate;
1-[2-tert-butyl-7-[(1-cyclopropyltetrazol-5-yl)methyl]pyrrolo[2,3-d]pyrimidin-4-yl]pyrrolidin-3-ol;
1-[2-tert-butyl-7-[(3R)-oxolan-3-yl]pyrrolo[2,3-d]pyrimidin-4-yl]pyrrolidin-3-ol;
1-[2-tert-butyl-7-[[3-(trifluoromethyl)-1H-pyrazol-4-yl]methyl]pyrrolo[2,3-d]pyrimidin-4-yl]pyrrolidin-3-ol;
2-tert-butyl-4-(3,3-difluoropyrrolidin-1-yl)-7-[[3-(trifluoromethyl)-1H-pyrazol-4-yl]methyl]pyrrolo[2,3-d]pyrimidine;
(3S)-1-[2-tert-butyl-7-[(2,3-dichlorophenyl)methyl]pyrrolo[2,3-d]pyrimidin-4-yl]pyrrolidin-3-ol;
(3S)-1-[2-tert-butyl-7-[(2-chloro-4-fluorophenyl)methyl]pyrrolo[2,3-d]pyrimidin-4-yl]pyrrolidin-3-ol;
(3S)-1-[2-tert-butyl-7-[[2-(trifluoromethyl)phenyl]methyl]pyrrolo[2,3-d]pyrimidin-4-yl]pyrrolidin-3-ol;
(3S)-1-[2-tert-butyl-7-[(2-methylsulfonylphenyl)methyl]pyrrolo[2,3-d]pyrimidin-4-yl]pyrrolidin-3-ol;
(3S)-1-[2-tert-butyl-7-[(2-chloropyridin-3-yl)methyl]pyrrolo[2,3-d]pyrimidin-4-yl]pyrrolidin-3-ol;
(3S)-1-[2-tert-butyl-7-[(3-chloropyridin-2-yl)methyl]pyrrolo[2,3-d]pyrimidin-4-yl]pyrrolidin-3-ol;
(3S)-1-[2-tert-butyl-7-[(4-methyl-1,2,5-oxadiazol-3-yl)methyl]pyrrolo[2,3-d]pyrimidin-4-yl]pyrrolidin-3-ol;
6-[2-tert-butyl-7-[(3-chloropyridin-2-yl)methyl]pyrrolo[2,3-d]pyrimidin-4-yl]-2-oxa-6-azaspiro[3.3]heptane; and
6-[2-tert-butyl-7-[(1-methyltetrazol-5-yl)methyl]pyrrolo[2,3-d]pyrimidin-4-yl]-2-oxa-6-azaspiro[3.3]heptane.

9. A compound according to claim 1 selected from 2-tert-butyl-4-(3,3-difluoropyrrolidin-1-yl)-7-[[2-(trifluoromethyl)phenyl]methyl]pyrrolo[2,3-d]pyrimidine;

2-tert-butyl-7-[(3-chloropyridin-2-yl)methyl]-4-(3,3-difluoropyrrolidin-1-yl)pyrrolo[2,3-d]pyrimidine;

3-[[2-tert-butyl-4-(3,3-difluoropyrrolidin-1-yl)pyrrolo[2,3-d]pyrimidin-7-yl]methyl]-4-methyl-1,2,5-oxadiazole;

1-[2-tert-butyl-7-[[2-(trifluoromethyl)phenyl]methyl]pyrrolo[2,3-d]pyrimidin-4-yl]pyrrolidin-3-ol;

1-[2-tert-butyl-7-[(2-chloropyridin-3-yl)methyl]pyrrolo[2,3-d]pyrimidin-4-yl]pyrrolidin-3-ol;

1-[2-tert-butyl-7-[(3-chloropyridin-2-yl)methyl]pyrrolo[2,3-d]pyrimidin-4-yl]pyrrolidin-3-ol;

(3S)-1-[2-tert-butyl-7-[(2,3-dichlorophenyl)methyl]pyrrolo[2,3-d]pyrimidin-4-yl]pyrrolidin-3-ol;

(3S)-1-[2-tert-butyl-7-[(2-chloro-4-fluorophenyl)methyl]pyrrolo[2,3-d]pyrimidin-4-yl]pyrrolidin-3-ol;

(3S)-1-[2-tert-butyl-7-[[2-(trifluoromethyl)phenyl]methyl]pyrrolo[2,3-d]pyrimidin-4-yl]pyrrolidin-3-ol;

(3S)-1-[2-tert-butyl-7-[(2-methylsulfonylphenyl)methyl]pyrrolo[2,3-d]pyrimidin-4-yl]pyrrolidin-3-ol;

(3S)-1-[2-tert-butyl-7-[(2-chloropyridin-3-yl)methyl]pyrrolo[2,3-d]pyrimidin-4-yl]pyrrolidin-3-ol;

(3S)-1-[2-tert-butyl-7-[(3-chloropyridin-2-yl)methyl]pyrrolo[2,3-d]pyrimidin-4-yl]pyrrolidin-3-ol; and (3S)-1-[2-tert-butyl-7-[(4-methyl-1,2,5-oxadiazol-3-yl)methyl]pyrrolo[2,3-d]pyrimidin-4-yl]pyrrolidin-3-ol.

10. A process for the preparation of a compound according to claim 1, comprising the reaction of a compound of formula (A)

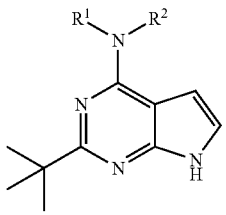

(A)

in the presence of X-A-R$^3$, wherein X is a leaving group and wherein A and R$^1$ to R$^3$ are as defined in claim 1.

11. A pharmaceutical composition comprising a compound of claim 1, and a therapeutically inert carrier.

* * * * *